United States Patent [19]

Abe et al.

[11] 3,935,193

[45] Jan. 27, 1976

[54] DIACYL PENICILLINS AND METHODS FOR THEIR PRODUCTION

[75] Inventors: Jinnosuke Abe, Shizuoka; Tetsuo Watanabe, Kanagawa; Teruo Take; Kentaro Fujimoto; Tadashiro Fujii; Kazuyoshi Nishiie, all of Shizuoka, all of Japan

[73] Assignee: Toyo Jozo Kabushiki Kaisha, Shizuoka, Japan

[22] Filed: Dec. 29, 1970

[21] Appl. No.: 102,556

[52] U.S. Cl............................... 260/239.1; 424/271
[51] Int. Cl............................................. C07d 99/16
[58] Field of Search................................. 260/239.1

[56] References Cited
UNITED STATES PATENTS

| | | | |
|---|---|---|---|
| 3,479,339 | 11/1969 | Holdrege | 260/239.1 |
| 3,567,709 | 3/1971 | Panina et al. | 260/239.1 |
| 3,594,367 | 7/1971 | Abe et al. | 260/239.1 |
| 3,668,200 | 6/1972 | Abe et al. | 260/239.1 |

*Primary Examiner*—Nicholas S. Rizzo
*Attorney, Agent, or Firm*—Young & Thompson

[57] ABSTRACT

Novel diacyl penicillins of the formula

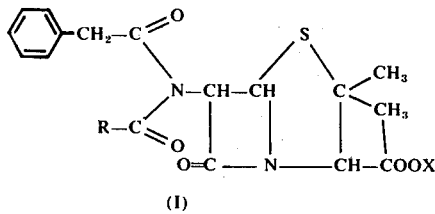

(I)

wherein R is alkyl, cycloalkyl, aryl, aralkyl, phenoxyalkyl, heterocyclic carboxyl excepting isoxazole carboxyl derivatives, or

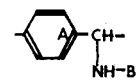

in which benzene ring A may optionally be substituted and B represents a protective group for the amino group, and X is a protective group for the carboxyl group, are produced by reacting a benzyl penicillin ester of the formula

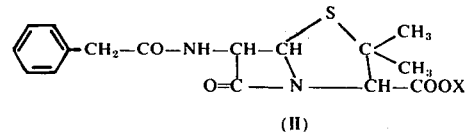

(II)

wherein X is as defined above, with a chlorinating agent in the presence of tertiary organic base to obtain an imide chloride group-incorporated compound of the formula

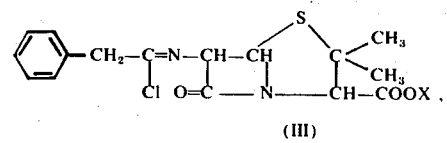

(III)

and then reacting the compound of the last-named formula with carboxylate of the formula

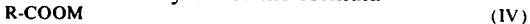

R-COOM        (IV)

wherein M is a metal atom, and R is as defined above.

4 Claims, No Drawings

DIACYL PENICILLINS AND METHODS FOR THEIR PRODUCTION

This invention relates to novel diacyl penicillins of the formula

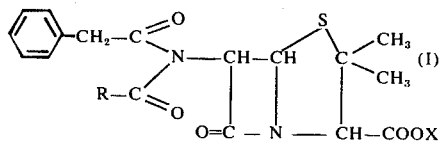

wherein X is a protective group for the carboxyl group, and R is alkyl, cycloalkyl, aryl, aralkyl, phenoxyalkyl, heterocyclic carboxyl excepting isoxazole carboxyl derivatives, or

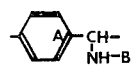

in which benzene ring A may optionally be substituted and B represents a protective group for the amino group, and methods for their production.

More particularly, the invention pertains to novel diacyl penicillins of Formula I and methods for their production, characterized in that a benzyl penicillin ester of the formula

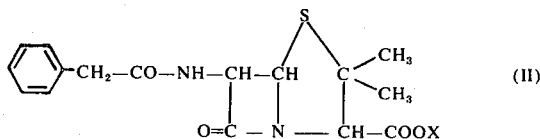

wherein X is as defined above is reacted with a chlorinating agent in the presence of a tertiary organic base to obtain an imide chloride group-incorporated compound of the formula

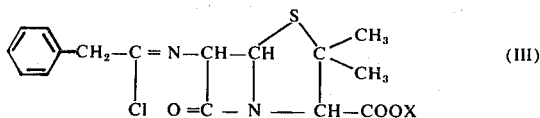

wherein X is as defined above; the compound of Formula III is reacted with carboxylate of the formula
R—COOM           (IV)

wherein M is a metal atom, and R is as defined previously, to obtain a diacyl penicillin ester of Formula I.

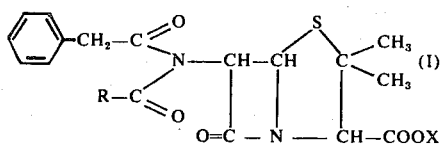

Heretofore, acyl derivatives of 6-aminopenicillanic acid, so called synthetic penicillins, have been prepared in such a manner that 6-aminopenicillanic acid is acylated according to such acylation process as acid halide process, acid anhydride process, mixed acid anhydride process, active ester process or process using a condensing agent. 6-aminopenicillanic acid used in the above processes, however, has to be prepared from fermentation broth in such a manner that benzylpenicillin or phenoxymethylpenicillin obtained by fermentation is deacylated with an enzyme produced by microorganisms, or 6-aminopenicillanic acid obtained by direct fermentation. According to these processes, however, the 6-aminopenicillanic acid should be isolated from the fermentation liquor; but the isolation step is troublesome because of the instability of the amphoteric water soluble compound. As a result, synthetic penicillins are expensive.

The present invention is characterized by the fact that penicillin derivatives are prepared chemically without using 6-aminopenicillanic acid but using as a starting material inexpensive benzylpenicillin obtainable by fermentation.

An object of the present invention is to provide novel diacyl penicillins and processes for preparing the same which are entirely different in inventive concept from the conventional processes for preparing penicillin derivatives by acylating 6-aminopenicillanic acid.

In the present invention, benzylpenicillin (hereinafter designated as PcG) obtained by fermentation is used as a starting material. However, the PcG is not used as it is but is used in the form of an ester such as benzylpenicillin ester of Formula II (hereinafter referred to as "PcG ester II") which is formed by introducing a protective group into the carboxyl group of PcG.

The carboxyl group of PcG is protected so that no side reaction will be brought about in the subsequent reaction, i.e. the reaction with a chlorinating agent.

The above-mentioned introduction of a protective group is carried out by introducing into a potassium or sodium salt of PcG obtained by fermentation a protective group such as is used ordinarily in the synthesis of peptides. Examples of protective groups which may be introduced are methyl, ethyl, t-butyl, p-methoxybenzyl, benzyl, p-nitrobenzyl, benzhydril, phenacyl, p-bromophenacyl and trimethylsilyl groups. Generally, however, the protective group introduced should be eliminated in the final step and therefore it is desirable to select a group capable of being easily eliminated without having any detrimental effect on the structure of penicillin. Favorable results are obtained by the use of such protective groups as, for example, benzyl, p-nitrobenzyl and benzhydril groups which can be easily eliminated by catalytic reduction, or phenacyl and p-bromophenacyl groups which can be eliminated with sodium thiophenoxide.

Generally, penicillins are unstable to acids and alkalis. Accordingly, when such a protective group which is eliminated by strong acid or alkali hydrolysis, e.g. a methyl, ethyl, t-butyl or p-methoxybenzyl group, has been introduced, the elimination thereof is difficult because a destruction in the structure of penicillin is brought about at the time of the elimination reaction. In the present invention, however, even when the final products, i.e. penicillin derivatives of Formula I (hereinafter designated as DA-Pc ester I) are in the form of esters having protective groups, the object of the invention can be accomplished without eliminating the protective groups so far as the protective groups are those of the kind which do not have pharmacologically detrimental effects. Examples of such protective groups are lower alkyl groups such as methyl, ethyl and the like groups.

In accordance with the present invention, the PcG ester II is reacted with a chlorinating agent to obtain an imide chloride group-incorporated compound of Formula III (hereinafter referred to as "the imide chloride III"). The above reaction is an application of a process in which an N-mono-substituted carboxylic acid amide is treated with a chlorinating agent to produce a corresponding imide chloride group-incorporated compound, and it is most preferable to adopt a process in which the reaction is effected, in the presence of a tertiary organic base, using $PCl_5$ or another such chlorinating agent as $PCl_3$, $POCl_3$, $COCl_2$, $SOCl_2$, etc. (South African patent 67/2927).

In the above reaction, it is preferable to use a suitable dry organic solvent. This solvent is desirably selected with a view to such factors as that it should not substantially detrimentally affect the reaction; that it should be able to solubilize the PcG ester II; and that it should be an organic solvent immiscible with water because, after the reaction, by-products formed are removed by washing. For example, benzene, toluene, chloroform, dichloromethane, dichloroethane, ethyl ether, or isopropyl ether are advantageously used.

If $PCl_5$, for example, is used in the above reaction as the chlorinating agent, $POCl_3$ and HCl are necessarily formed. In case a hydrochloride of the tertiary organic base has precipitated in the reaction liquid, it is previously removed by filtration and, since the imide chloride III obtained is relatively stable to water, $POCl_3$ can be removed from the reaction liquid by washing with an aqueous weakly alkali solution, e.g. an aqueous sodium or potassium bicarbonate solution. It is desirable that the above washing operation be carried out as quickly as possible and, after the washing, the reaction mother liquor be immediately dried by addition of anhydrous sodium sulfate or magnesium sulfate.

In view of the fact that compounds having imide chloride groups are generally unstable to water, it is an entirely surprising fact that the imide chloride III obtained by the aforesaid reaction is relatively stable to water. Further, it brings about extremely favorable results for the present invention that, by the abovementioned operation, a reaction mother liquor containing the imide chloride III can be obtained in a stable state.

In the above-mentioned reaction mother liquor, the unreacted tertiary organic base remains as it is. This base can be easily removed from the reaction mother liquor as a water-soluble acid addition salt by washing the liquor with a dilute acid. However, the imide chloride III is unstable to acids and therefore it is desirable that said base not be removed. As the tertiary organic base employed in the present invention, therefore, the use of such a weakly basic base as pyridine, quinoline, dimethylaniline or the like, for example, gives favorable results. This is because in the subsequent reaction, i.e. in the step where the imide chloride III is reacted with a carboxylate of Formula IV (hereinafter referred to as "the carboxylate IV") to form a DA-Pc ester of Formula I, if a tertiary organic amine high in basicity, e.g. triethylamine or the like, is present, there is grave danger that a stereochemical rearrangement (epimerization) will take place in the hydrogen atom at the 6-position of the penicillin nucleus; but in the presence of such a weakly basic base as pyridine, there is little danger of epimerization.

The imide chloride III contained in the above-mentioned reaction mother liquor may be reacted as it is, without any further purification, with the carboxylate IV. Alternatively, it may be reacted with the carboxylate IV after concentrating the reaction mother liquor and dispersing the concentrate in another suitable solvent, e.g. benzene, toluene, chloroform, dichloromethane, dichloroethane, ethyl ether, isopropyl ether, tetrahydrofuran or dioxane. However, an aqueous solution treatment is effected after the reaction and therefore it is advantageous to use a water-immiscible solvent.

Examples of the carboxylate IV to be reacted with the imide chloride III are metal salts, such as potassium, sodium, lithium and silver salts, of fatty acid, alicyclic carboxylic acid, aromatic acid, aromatic fatty acid, phenoxy fatty acid, carboxylic acid containing heterocyclic group such as heterocyclic carboxylic acid excepting isoxazole derivatives, heterocyclic fatty acid, heterocyclic fatty acid intersepted by oxygen or sulfur atom and amino group protected phenylglycine. These compounds may optionally be substituted as far as non-detrimental effect is revealed in the reaction with imide chloride III. Examples of the said substitution groups are alkyl, alkoxy, nitro, haloalkyl, alkylthio or arylthio group, or halogen atom. The substituent such as amino or carboxyl group in carboxylic acid which is in danger of reaction with imidechloride III, however, may be protected by protective group to prevent such the danger.

Examples of the carboxylate IV hereinbefore are metal salts, such as potassium, sodium, lithium and silver salts, of acetic acid, propionic acid, butylic acid, iso-butylic acid, valeric acid, iso-valeric acid, pivalic acid, caproic acid, heptanoic acid, caprylic acid, pelargonic acid, capric acid, undecylenic acid, lauric acid, stearic acid, 2-ethylhexanoic acid, alpha-chloro isobutylic acid, alpha-chloro valeric acid, alpha-chlorohexanoic acid, acrylic acid, crotonic acid, vinyl acetic acid, pentenoic acid, such as allylacetic acid, angelic acid and tiglic acid, hydrosorbic acid, pyrotérebic acid, heptenoic acid, octenoic acid, cyclohexanecarboxylic acid, cyclopentanecarboxylic acid, cyclopropylacetic acid, cyclobutylacetic acid, cyclopentylacetic acid, cyclohexylacetic acid, benzoic acid, toluic acid, alpha-naphthoic acid, beta-naphthoic acid, 2-methoxynaphthoic acid, 2,8-dimethoxy-1-naphthoic acid, p-chlorobenzoic acid, p-chloro-o-toluic acid, 3,4-dichlorobenzoic acid, p-methoxybenzoic acid, phenylacetic acid, betaphenylpropionic acid, triphenylacetic acid, alpha-methoxyphenyacetic acid, alpha-methoxy-3,4-dichlorophenylacetic acid, 2,4-dichloroacetic acid, 3,4-dichloroacetic acid, alpha-N-carbobenzoxy-aminophenyacetic acid, alpha-p-nitrobenzenesulfonyl amino phenylacetic acid, alpha-trityl-amino-phenylacetic acid, phenylmalonic acid monobenzyl ester, phenylmalonic acid mono-p-nitrobenzyl ester, alpha-acetoxyphenylacetic acid, alpha-(2,4-dichlorophenoxy)-phenylacetic acid, alpha-chlorophenylacetic acid, phenoxyacetic acid, alpha-phenoxypropionic acid, alpha-phenoxy-iso-valeric acid, alphaphenoxy-iso-butylic acid, alpha-(2,4-dichlorophenoxy)-propionic acid, alphaphenoxyphenylacetic acid, alpha-(p-t-butylphenoxy)-propionic acid, 2,4,-dichlorophenoxy-n-butylic acid, alpha-(3,4-dimethoxyphenoxy)-propionic acid, alpha-(3-methylphenoxy)-propionic acid, alpha-(2- trifluoromethylphenoxy)-propionic acid, alpha-(4- chlorophenoxy)-propionic acid, alpha(p-methoxyphenoxy)-propionic acid, alpha-iso-propylthio-iso-valeric acid, alpha-ethylthiopropionic acid, alpha-phenylthiopropionic acid, alpha-o-trylthiopropionic acid or the like.

Further examples of the aforesaid carboxylic acid IV are metal salts, such as potassium, sodium, lithium and silver salts, of 1-methyl-3-phenylindole-2-carboxylic acid, 1,3-diphenylindole-2-carboxylic acid, 1.3-dimethylindole-2-carboxylic acid, 2,4-dichloro-6-methylpyridine-3-carboxylic acid, 3-ethoxy-2-methylquinoline-4-carboxylic acid, 3,7-dimethoxycoumarine4-carboxylic acid, 3-methoxypicolinic acid, 2-phenylpyrazine-3-carboxylic acid, 1-phenyl-3-methyl-4-bromopyrazole-5-carboxylic acid, 1-phenyl-4-methylpyrazole-5-carboxylic acid, 1-(p-chlorophenyl)-3-methyl-4-bromopyrazole-5-carboxylic acid, 1-(p-chlorophenyl)-3-methyl-4-chloropyrazole-5-carboxylic acid, 1-(p-bromophenyl)-3-methyl-4-bromopyrazole-5-carboxylic acid, 1-(2',6'-dichlorophenyl)-4-methylpyrazole-5-carboxylic acid, 1-(2',4',6'-trichlorophenyl)-4-methylpyrazole-5-carboxylic acid, 1-cyclohexyl-3-methyl-4-chloropyrazole-5-carboxylic acid, 1-cyclohexyl-4-methylpyrazole-5-carboxylic acid, 1,2,3-thiadiazole-4-carboxylic acid, 2-methyl-5-phenylthiazole-4-carboxylic acid, 5-(o-chlorophenyl)-2-methylthiazole4-carboxylic acid, 5-phenylthiazole-4-carboxylic acid, 3-(o-chlorophenyl)5-methoxyisothiazole-4-carboxylic acid, 5-methoxy-3-phenylisothiazole-4-carboxylic acid, 3-phenyl-5-methylisothiazole-4-carboxylic acid, 3-(2',6'dichlorophenyl)-5-methylisothiazole-4-carboxylic acid, 3-(o-chlorophenyl)5-methylisothiazole-4-carboxylic acid, thiophene-2-acetic acid, thiophene3-acetic acid, 3-pyridyl acetic acid, 6-methyl-3-pyridyl acetic acid, alpha-methoxy-5-chloro-2-thienyl acetic acid, furan-2-acetic acid, alphamethoxy-2-furyl acetic acid, alpha-N-carbobenzoxyamino-2-thienyl acetic acid, alpha-N-carbobenzoxyamino-3-thienyl acetic acid, 2-thienylmalonic acid monobenzyl ester, 3-thienylmalonic acid monobenzyl ester, isothiazole-3-acetic acid, isothiazole-4-acetic acid, isothiazole-5-acetic acid, 4-chloroisothiazole-3-acetic acid, 4-methyl isothiazole-3-acetic acid, 1,2,5,-thiadiazole-3-acetic acid, isatin-1-acetic acid, 5-methyl isatin-1-acetic acid, 5-chloroisatin-1-acetic acid, 6-methyl isatin-1-acetic acid, 5-methoxyisatin-1-acetic acid, 5,7-dimethyl isatin-1-acetic acid, 3-methyl furazan-4-acetic acid, 3-methoxy furazan-4-acetic acid, tetrazole-4-carboxylic acid, 2-thienyloxy acetic acid, 3-thienyloxy acetic acid, 5-methyl-2-thienyloxy acetic acid, 2,3-dimethyl-4-thienyloxy acetic acid, 3-thienyloxy propionic acid or the like.

Still further examples of the carboxylic acid IV hereinbefore are metal salts, such as potassium, sodium, lithium and silver salts, of substituted or non-substituted phenylglycine in which amino group is protected. A phenyl group of phenylglycine may be substituted by substituent, having non detrimental effect at reaction with imide chloride, such as alkyl, alkoxy, nitro, halogen, haloalkyl, alkylthio and arylthio. In case of a group such as amino or hydroxy substituted in benzene ring which fears to react with imide chloride, phenyl group may be substituted if the said substituent is protected by protective group which do not react with imide chloride. When, in that case, eliminating the said protective group, the eliminating condition should be selected without having any destructive effect to the structure of penicillin.

The above-mentioned introduction of a protective group to amino group in the carboxylate is carried out by introducing a protective group such as is used ordinarily in the synthesis of peptides. Examples of protective groups which may be introduced are carbobenzoxy, p-nitrocarbobenzoxy, carboaryloxy, p-toluenesulfonyl, phthalyl, trityl, benzyl,dibenzyl, benzylsulfonyl, o-nitrophenylsulfenyl, trifuluoroacetyl, chloroacetyl, formyl and o-nitrophenoxyacetyl. Generally, however, the protective group introduced should be eliminated in the final step and therefore it is desirable to select a group capable of being easily eliminated without having any detrimental effect on the structure of penicillin. The carboxylate IV may be added directly to the reaction mother liquor containing the imide chloride III or may be used in the form of a suspension in the same solvent as in the reaction mother liquor. In this case, if a tertiary organic base of high basicity such as triethylamine or the like is used in place of the carboxylate IV, there is grave danger that the resulting DA-Pc ester I will cause epimerization at the hydrogen atom in the 6-position of the penicillin nucleus, as mentioned above. However, when a metal salt such as a potassium, sodium, lithium or silver salt is used, said epimerization can be prevented or the degree of epimerization can be greatly reduced.

Theoretically, the quantitative proportion of the carboxylate IV is equimolar to the imide chloride III. After the reaction, however, the removal of unreacted carboxylate IV is easier than the removal of unreacted imide chloride III. Ordinarily, therefore, the carboxylate IV id used somewhat in excess.

The above-mentioned reaction easily progresses at room temperature; however in case of low reaction rate, it is acceptable to heat to at most about 40°–50° C., being careful not to decompose the imide chloride III or produced DA-Pc ester I by sudden heating or overheating.

According to the above reaction, there is obtained the DA-Pc ester I. In separating this reaction product, the reaction liquid is washed with an aqueous dilute acid solution, an aqueous dilute alkali solution, and water, in this order, to remove remaining tertiary organic base, e.g. pyridine or the like, and unreacted carboxylate IV, and then the reaction mother liquor is concentrated and is subjected to alumina or silica gel-column chromatography using a solvent of benzene-ethyl acetate or the like system, whereby only the desired DA-Pc ester I is first eluted. When the eluted fraction is subjected to freeze-drying or the like, the product can be easily isolated.

The thus-obtained DA-Pc ester I is a novel compound, and further, by dephenylacetylation and de-esterification reactions, and elimination of protective group for amino group, if necessary, there can be prepared the important antibacterial agents comprising the phenoxyethyl penicillin, phenoxypropyl penicillin, ampicillin and the like of the formula

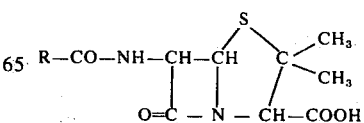

wherein R is defined previously. Thus the synthetic penicillins are prepared by chemical reactions only, without using 6-aminopenicillanic acid but using PcG obtained by fermentation; and DA-Pc ester I prepared by the present invention is, therefore, a very important intermediate of a process for the production of synthetic penicillins. Also, novel penicillins can be prepared by deesterification of DA-Pc ester I (i.e. removal of X in DA-Pc ester I).

The present invention will be illustrated in detail below with reference to various examples, it being understood that the various reaction operations and compounds which may be employed in the present invention are not limited to those shown in these examples.

Example 1

Preparation of N-(alpha-phenoxypropionyl)-benzyl-penicillin-p-nitrobenzyl eater:

46.9 g. (0.1 mole) of the PcG-p-nitrobenzyl ester was dissolved in 200 ml. of dry benzene. To this solution was added 32.4 ml. (0.4 mole) of dry pyridine while cooling to 0°C. with stirring. Thereafter, a solution of 21.8 g. (0.105 mole) of $PCl_5$ in 200 ml. of dry benzene was added dropwise over a period of about 30 minutes. Subsequently, the liquid was reacted for 1 hour while maintaining the temperature thereof at 0°C.

After the reaction, precipitated pyridine hydrochloride was removed by filtration, and the reaction mother liquor was quickly washed with saturated sodium chloride solution, with saturated sodium bicarbonate solution, and with saturated sodium chloride solution, in this order, to remove unreacted $PCl_5$ and by-product $POCl_3$. The washed benzene solution was dried with anhydrous silica gel, and then 20.3 g. (0.1 mole) of potassium alpha-phenoxypropionate was added, and was reacted at 30°C. for over night.

The reaction liquid was washed with 0.5 N hydrochloric acid, with a 1 N aqueous sodium bicarbonate solution and with an aqueous saturated sodium chloride solution, in this order, to remove pyridine and unreacted alpha-phenoxypropionic acid, and the reaction mother liquor was dried with anhydrous silica gel and was then concentrated under reduced pressure. Subsequently, the concentrate was charged on a column comprising 500 g. of silica gel (60–80 mesh) and was eluted with anhydrous benzene-ethyl acetate (10 : 1), whereby the first eluted fraction contained a desired N-(alpha-phenoxypropionyl)-benzylpenicillin-p-nitrobenzyl ester. This fraction was collected and was freeze-dried to obtain 30.95 g. of a freeze-dried product, yield 50.1%.

Elementary analysis for $C_{32}H_{31}O_8N_3S$:

|  | C% | H% | N% |
|---|---|---|---|
| Found: | 61.98 | 5.15 | 6.84 |
| Calculated: | 62.23 | 5.06 | 6.80 |

EXAMPLE 2

Preparation of N-(alpha-phenoxy iso-butylyl)-benzylpenicillin-p-nitrobenzyl ester:

Example 1 was repeated, except that the potassium alpha-phenoxy isobutylate was used in place of the potassium alpha-phenoxypropionate, to obtain 29.3 g. of N-(alpha-phenoxy iso-butylyl)-benzylpenicillin-p-nitrobenzyl ester, yield 46.4%.

Elementary analysis for $C_{33}H_{33}O_8N_3S$:

|  | C% | H% | N% |
|---|---|---|---|
| Found: | 62.51 | 5.36 | 6.80 |
| Calculated: | 62.75 | 5.27 | 6.65 |

EXAMPLE 3

Preparation of N-(phenylacetyl)-benzylpenicillin-p-nitrobenzyl ester:

Example 1 was repeated, except that sodium phenylacetate was used in place of the potassium alpha-phenoxypropionate, to obtain 20.4 g. of lyophilized N-(phenylacetyl)-benzylpenicillin-p-nitrobenzyl ester, yield 34.8%.

Elementary analysis for $C_{31}H_{29}O_7N_3S$:

|  | C% | H% | N% |
|---|---|---|---|
| Found: | 63.18 | 5.08 | 7.09 |
| Calculated: | 63.37 | 4.97 | 7.15 |

EXAMPLE 4

Preparation of N-phenoxyacetyl benzylpenicillin-p-nitrobenzyl ester:

Example 1 was repeated, except that potassium phenoxyacetate was used in place of the potassium alpha-phenoxypropionate, to obtain 26.1 g. of lyophilized N-phenoxyacetyl benzylpenicillin-p-nitrobenzyl ester, yield 43.2%.

Elementary analysis for $C_{31}H_{29}O_8N_3S$:

|  | C% | H% | N% |
|---|---|---|---|
| Found: | 61.93 | 4.80 | 7.08 |
| Calculated: | 61.69 | 4.84 | 6.96 |

EXAMPLE 5

Preparation of N-(2-ethylhexanoyl)-benzylpenicillin phenacyl ester:

22.62 g. (0.05 mole) of PcG phenacyl ester was dissolved in 75 ml. of dry benzene. To this solution was added 16.2 ml. (0.2 mole) of dry pyridine while cooling to 0°C. with stirrig. Thereafter, a solution of 10.8 g. (0.05 mole) of $PCl_5$ in 75 ml. of dry benzene was added dropwise over a period of about 30 minutes. Subsequently, the liquid was reacted for 1 hour while maintaining the temperature thereof at 0°C.

After the reaction, precipitated pyridine hydrochloride was removed by filtration, and the reaction mother liquor was quickly washed with saturated sodium chloride solution, with saturated aqueous sodium bicarbonate solution and with saturated sodium chloride solution, in this order, to remove unreacted $PCl_5$ and by-product $POCl_3$. The washed benzene solution was dried with anhydrous silica gel, and then 8.3 g. (0.05 mole) of sodium 2-ethylhexanoate was immediately added. The reaction mixture was reacted for over night at 30°C.

The reaction mixture was washed with 0.5 N hydrochloric acid, with 1 N aqueous sodium bicarbonate solution, and with saturated sodium chloride solution, in this order, and the reaction mother liquor was dried with anhydrous silica gel, and was then concentrated in vacuo.

Subsequently, the concentrate was charged on 250 g. of silica gel column (60–80 mesh) and was eluted with anhydrous benzene-ethyl acetate (10 : 1), whereby the first eluted fraction contained a desired N-(2-ethylhexanoyl)-benzylpenicillin phenacyl ester. This fraction was collected and freeze-dried to obtain 20.0 g. of freeze-dried product, yield 69.2%.

The product was assayed by silica gel thin-layer chromatography with developing a mixture of benzene-ethyl acetate (3:1) to shown one spot of $R_f$ value 0.75.

Elementary analysis for $C_{32}H_{38}O_6N_2S$ Br:

|  | C% | H% | N% |
| --- | --- | --- | --- |
| Found: | 66.81 | 6.58 | 4.79 |
| Calculated: | 66.42 | 6.62 | 4.84 |

EXAMPLE 6

Preparation of N-pivaloyl benzylpenicillin phenacyl ester:

Example 5 was repeated, except that the potassium pivalate was used in place of the sodium 2-ethylhexanoate, to obtain 13.1 g. of lyophilized N-pivaloyl benzylpenicillin phenacyl ester, yield 48.8%.

The Rf value of the product on silica gel thin-layer chromatogram is 0.778.

EXAMPLE 7

Preparation of N-caproyl benzylpenicillin phenacyl ester:

Example 5 was repeated, except that potassium n-caprylate was used in place of the sodium 2-ethyl hexanoate, to obtain 12.7 g. of lyophilized N-n-caproyl benzylpenicillin phenacyl ester, yield 43.9%.

The Rf value of the product on silica gel thin-layer chromatogram is 0.77.

EXAMPLE 8

Preparation of N-cyclohexane carbonyl benzylpenicillin phenacyl ester:

Example 5 was repeated, except that sodium cyclohexane carboxylate was used in place of the sodium 2-ethyl hexanoate, to obtain 10.65 g. of lyophilized N-cyclohexane carbonyl benzylpenicillin phenacyl ester, yield 37.8%.

Elementary analysis for $C_{31}H_{34}O_6N_2S$:

|  | C% | H% | N% |
| --- | --- | --- | --- |
| Found: | 65.94 | 6.16 | 4.90 |
| Calculated: | 66.18 | 6.10 | 4.98 |

EXAMPLE 9

Preparation of N-benzoyl benzylpenicillin phenacyl ester:

Example 5 was repeated, except that sodium benzoate was used in place of sodium 2-ethyl hexanoate, to obtain 12.4 g. of lyophilized N-benzoyl benzylpenicillin phenacyl ester, yield 44.5%

The Rf value of the product on silica gel thin-layer chromatogram is 0.696.

EXAMPLE 10

Preparation of N-(alpha-N'-carbobenzoxy-aminophenylacetyl)benzylpenicillin phenacyl ester:

Example 5 was repeated, except that the potassium alpha-N-carbobenzoxyamino-phenylacetate was used in place of sodium 2-ethyl hexanoate, to obtain N-(alpha-carbobenzoxy-amino-phenylacetyl)-benzylpenicillin phenacyl ester. The dried product is recrystalyzed from the mixture of ethylacetate-petroleum ether to obtain 21.3 g. of crystaline product having m.p. 187° – 188°C., yield 59.2%.

Elementary analysis for $C_{40}H_{37}O_8N_3S$:

|  | C% | H% | N% |
| --- | --- | --- | --- |
| Found: | 66.74 | 5.02 | 5.81 |
| Calculated: | 66.75 | 5.18 | 5.84 |

Peaks of NMR (Nuclear Magnetic Resonance) spectra of the product in $CDCl_3$ are as follows; 1.50 (S,3H), 1.60 (S, 3H), 4.03 (S, 2H), 4.60 (S, 1 H), 4.94 (S,3H), 5.08 (d, J=4.0 cps, 1 H), 5.18 (d, J= 16.0 cps, 1 H), 5.30 (S, 1 H), 5.53 (d, J=4.0 cps, 1 H), 5.54 (d, J=16.0 cps, 1 H), 7.20 – 7.95 (20 H).

EXAMPLE 11

Preparation of N-(alpha-benzyloxy carbonyl-phenylacetyl)-benzylpenicillin phenacyl ester:

Example 5 was repeated, except that potassium phenylmalonate monobenzyl ester was used in place of the sodium 2-ethylhexanoate, to obtain 10.8 g. of lyophilized N-alpha-benzyloxy carbonyl-phenylacetyl)-benzylpenicillin phenacyl ester, yield 30.3%.

Elementary analysis for $C_{41}H_{38}O_8N_2S$;

|  | C% | H% | N% |
| --- | --- | --- | --- |
| Found: | 68.67 | 5.44 | 3.83 |
| Calculated: | 68.51 | 5.33 | 3.90 |

EXAMPLE 12

Preparation of N-[1-(2',6'-dichlorophenyl)-4-methylpyrazole-5'-carbonyl]benzylpenicillin phenacyl ester:

22.62 g. (0.05 mole) of PcG phenacyl ester was dissolved in 75 ml. of dry benzene. To this solution was added 16.2 ml. (0.2 mole) of dry pyridine while cooling to 0°C. with stirring. Thereafter, a solution of 10.8 g. (0.05 mole) of $PCl_5$ in 75 ml. of dry benzene was added dropwise over a period of about 30 minutes. Subsequently, the liquid was reacted for 1 hour while maintaining the temperature thereof at 0°C.

After the reaction, precipitated pyridine hydrochloride was removed by filtration, and the reaction mother liquor was quickly washed with saturated sodium chloride solution, with saturated aqueous sodium bicarbonate solution and with saturated sodium chloride solution, in this order, to remove unreacted $PCl_5$ and by-product $POCl_3$. The washed benzene solution was dried with anhydrous silica gel while ice-cooling, and then 15.5 g. (0.05 mole) of potassium 1-(2',6'-dichlorophenyl)-4-methylpyrazole-5-carboxylate was immediately added. The reaction mixture was reacted for over night at 30°C.

The reaction mixture was washed with 0.5 N hydrochloric acid, with 1 N aqueous sodium bicarbonate solution, with saturated sodium chloride solution, and with water, in this order, and the reaction mother liquor was dried with anhydrous silica gel, and was then concentrated in vacuo.

Subsequently, the concentrate was charged on 250 g. of silica gel column (60 – 80 mesh) and was eluted with anhydrous benzene-ethyl acetate (10 : 1), whereby the first eluted fraction contained a desired N- [1(2',6'-dichlorophenyl)-4-methylpyrazole-5-carbonyl]-benzylpenicillin phenacyl ester. This fraction was collected and freeze-dried to obtain 15.7 g. of freeze-dried product, yield 44.5%.

Elementary analysis for $C_{35}H_{30}O_6N_4SCl_2$:

|  | C% | H% | N% |
|---|---|---|---|
| Found: | 60.00 | 4.23 | 7.98 |
| Calculated: | 59.58 | 4.29 | 7.94 |

EXAMPLE 13

Preparation of N-[1-(p-chlorophenyl)-3-methylpyrazole-5-carbonyl]-benzylpenicillin phenacyl ester:

Example 12 was repeated, except that potassium 1-(p-chlorophenyl)-3-methylpyrazol-5-carboxylate was used in place of potassium 1-(2',6'-dichlorophenyl)-4-methylpyrazole-5-carboxylate, to obtain 16.31 g. of lyophilized N-[1-(p-chlorophenyl)-3-methylpyrazole-5-carbonyl]-benzylpenicillin phenacyl ester, yield 48.6%.

Elementary analysis for $C_{35}H_{31}O_6N_4SCl$:

|  | C% | H% | N% |
|---|---|---|---|
| Found: | 62.51 | 4.73 | 8.26 |
| Calculated: | 62.64 | 4.66 | 8.35 |

EXAMPLE 14

Preparation of N-(1-phenyl-4-methylpyrazole-5-carbonyl)-benzylpenicillin phenacyl ester:

Example 12 was repeated, except that potassium 1-phenyl-4-methylpyrazole-5-carboxylate was used in place of potassium 1-(2',6'-dichlorophenyl)-4-methylpyrazole-5-carboxylate, to obtain 15.98 g. of lyophilized N-(1-phenyl-4-methylpyrazole-5-carbonyl)-benzylpenicillin phenacyl ester, yield 50.2%.

Elementary analysis for $C_{35}H_{32}O_6N_4S$:

|  | C% | H% | N% |
|---|---|---|---|
| Found: | 65.81 | 5.13 | 8.78 |
| Calculated: | 66.03 | 5.07 | 8.80 |

EXAMPLE 15

Preparation of N-(1,3-dimethylindole-2-carbonyl)-benzylpenicillin phenacyl ester:

Example 12 was repeated, except that potassium 1,3-dimethylindole2-carboxylate was used in place of potassium 1-(2',6'-dichlorophenyl)4-methylpyrazole-5-carboxylate, to obtain 12.0 g. of lyophilized N-(1,3,-dimethylindole-2-carbonyl)-benzylpenicillin phenacyl ester, yield 62.0%.

Elementary analysis for $C_{35}H_{33}O_6N_3S$:

|  | C% | H% | N% |
|---|---|---|---|
| Found: | 67.43 | 5.26 | 6.82 |
| Calculated: | 67.41 | 5.33 | 6.74 |

EXAMPLE 16

Preparation of N-(2-methyl-5-phenylthiazole-4-carbonyl)-benzylpenicillin phenacyl ester:

Example 12 was repeated, except that potassium 2-methyl-5-phenylthiazole-4-carboxylate was used in place of 1-(2',6'-dichlorophenyl)-4-methylpyrazole-5-carboxylate, to obtain 22.26 g. of lyophilized N-(2-methyl-5-phenylthiazole-4-carbonyl)-benzylpenicillin phenacyl ester, yield 69.8%.

Elementary analysis for $C_{35}H_{31}O_7N_3S$:

|  | C% | H% | N% |
|---|---|---|---|
| Found: | 66.20 | 4.81 | 6.49 |
| Calculated: | 65.93 | 4.90 | 6.59 |

EXAMPLE 17

Preparation of N-[5-(o-chlorophenyl)-2-methylthiazole-4-carbonyl]-benzylpenicillin phenacyl ester:

Example 12 was repeated, except that potassium 5-(o-chlorophenyl)-2-methylthiazole-4-carboxylate was used in place of potassium 1-(2',6'-dichlorophenyl)-4-methylpyrazole-5-carboxylate, to obtain 20.26 g. of lyophilized N-[5-(o-chlorophenyl)-2-methylthiazole-4-carbonyl]-benzylpenicillin phenacyl ester, yield 60.3%.

Elementary analysis for $C_{35}H_{30}O_7N_3SCl$:

|  | C% | H% | N% |
|---|---|---|---|
| Found: | 62.42 | 4.53 | 6.33 |
| Calculated: | 62.55 | 4.50 | 6.25 |

EXAMPLE 18

Preparation of N-[5-(2',6'-dichlorophenyl)-3-methylisothiazole-4-carbonyl]-benzylpenicillin phenacyl ester:

Example 12 was repeated, except that potassium 5-(2',6'-dichlorophenyl)-3-methylisothiazole-4-carboxylate was used in place of potassium 1-(2',6'-dichlorophenyl)-4-methylpyrazole-5-carboxylate, to obtain 17.9 g. of lyophilized N-[5-(2',6'-dichlorophenyl)-3-methylisothiazole-4-carbonyl]-benzylpenicillin phenacyl ester; yield 50.4%.

Elementary analysis for $C_{34}H_{29}O_6N_3S_2Cl_2$:

|  | C% | H% | N% |
|---|---|---|---|
| Found: | 57.77 | 4.04 | 5.99 |
| Calculated: | 57.47 | 4.11 | 5.91 |

EXAMPLE 19

Preparation of N-[5-(o-chlorophenyl)-3-methylisothiazole-4-carbonyl]-benzylpenicillin phenacyl ester:

Example 12 was repeated, except that potassium 5-(o-chlorophenyl)-3-methylisothiazole-4-carboxylate was used in place of potassium 1-(2',6'-dichlorophenyl)-4-methylpyrazole-5-carboxylate, to obtain 21.5 g. of lyophilized N-[5-(o-chlorophenyl)-3-methylisothiazole-4-carbonyl]-benzylpenicillin phenacyl ester, yield 63.6%.

Elementary analysis for $C_{34}H_{30}O_6N_3S_2Cl$:

|  | C% | H% | N% |
|---|---|---|---|
| Found: | 60.15 | 4.39 | 6.30 |
| Calculated: | 60.40 | 4.47 | 6.22 |

EXAMPLE 20

Preparation of N-(3-methyl-5-phenyl-isothiazole-4-carbonyl)-benzylpenicillin phenacyl ester:

Example 12 was repeated, except that potassium 3-methyl-5-phenylisothiazole-4-carboxylate was used in place of potassium 1-(2',6'-dichlorophenyl)-4-methylpyrazole-5-carboxylate, to obtain 22.4 g. of lyophilized N-(3-methyl-5-phenylisothiazole-4-carbonyl)-benzylpenicillin phenacyl ester, yield 70.0%.

Elementary analysis for $C_{34}H_{30}O_6N_3S_2$:

|  | C% | H% | N% |
|---|---|---|---|
| Found: | 64.02 | 4.63 | 6.54 |
| Calculated: | 63.75 | 4.72 | 6.56 |

EXAMPLE 21

Preparation of N-(thiophene-2-acetyl)-benzylpenicillin phenacyl ester:

22.62 g. (0.05 mole) of PcG phenacyl ester was dissolved in 75 ml. of dry benzene. To this solution was added 16.2 ml. (0.2 mole) of dry pyridine while cooling to 0°C. with stirring. Thereafter, a solution of 10.8 g. (0.05 mole) of $PCl_5$ in 75 ml. of dry benzene was added dropwise over a period of about 30 minutes. Subsequently, the liquid was reacted for 1 hour while maintaining the temperature thereof at 0°C.

After the reaction, precipitated pyridine hydrochloride was removed by filtration, and the reaction mother liquor was quickly washed with saturated sodium chloride solution, with saturated aqueous sodium bicarbonate solution and with saturated sodium chloride solution, in this order, to remove unreacted $PCl_5$ and by-product $POCl_3$. The washed benzene solution was dried with anhydrous silica gel, and then 9.0 g. (0.05 mole) of potassium thiophene-2-acetate was immediately added. The reaction mixture was reacted for over night at 30°C.

The reaction mixture was washed with 0.5 N hydrochloric acid, with 1 N aqueous sodium bicarbonate solution, and with saturated sodium chloride solution, in this order, and the reaction mother liquor was dried with anhydrous silica gel, and was then concentrated in vacuo.

Subsequently, the concentrate was charged on 250 g. of silica gel column (60 – 80 mesh) and was eluted with anhydrous benzene-ethyl acetate (10 : 1), whereby the first eluted fraction contained a desired N-(thiophene-2-acetyl)-benzylpenicillin phenacyl ester. This fraction was collected and freeze-dried to obtain 14.07 g. of freeze-dried product, yield 48.8%.

Elementary analysis for $C_{30}H_{28}O_6N_2S_2$:

|  | C% | H% | N% |
|---|---|---|---|
| Found: | 62.22 | 4.96 | 4.80 |
| Calculated: | 62.50 | 4.90 | 4.86 |

EXAMPLE 22

Preparation of N-(thiophene-3-acetyl)-benzylpenicillin phenacyl ester:

Example 21 was repeated, except that potassium thiophene-3-acetate was used in place of potassium thiophene-2-acetate, to obtain 16.46 g. of freeze-dried N-(thiophene-3-acetyl)-benzylpenicillin phenacyl ester, yield 57.1%.

Elementary analysis for $C_{38}H_{28}O_6N_2S_2$:

|  | C% | H% | N% |
|---|---|---|---|
| Found: | 62.59 | 4.88 | 4.80 |
| Calculated: | 62.50 | 4.90 | 4.86 |

EXAMPLE 23

Preparation of N-(alpha-N'-carbobenzoxy-amino-3-thienylacetyl)-benzylpenicillin phenacyl ester:

Example 21 was repeated, except that potassium alpha-N-carbobenzoxy-amino-3-thienyl acetate was used in place of potassium thiophene-2-acetate, to obtain 13.8 g. of freeze-dried product of N-(alpha-N'-carbobenzolxy-amino-3-thienylacetyl)-benzylpenicillin phenacyl ester, yield 38.1%.

Elementary analysis for $C_{38}H_{35}O_8N_3S_2$:

|  | C% | H% | N% |
|---|---|---|---|
| Found: | 63.03 | 4.79 | 5.77 |
| Calculated: | 62.81 | 4.86 | 5.78 |

EXAMPLE 24

Preparation of N-(isothiazole-3-acetyl)-benzylpenicillin phenacyl ester:

Example 21 was repeated, except that potassium isothiazole-3-acetate was used in place of potassium thiophene-2-acetate, to obtain 14.0 g. of freeze-Dried N-(isothiazole-3-acetyl)-benzylpenicillin phenacyl ester, yield 48.5%.

Elementary analysis for $C_{29}H_{27}O_6N_3S_2$:

|  | C% | H% | N% |
|---|---|---|---|
| Found: | 60.08 | 4.74 | 7.34 |
| Calculated: | 60.31 | 4.71 | 7.28 |

EXAMPLE 25

Preparation of N-(4-methylisothiazole-3-acetyl)-benzylpenicillin phenacyl ester:

Example 21 was repeated, except that potassium 4-methylisothiazole-3-acetate was used in place of potassium thiophene-2-acetate, to obtain 14.6 g. of freeze-dried N-(4-methylisothiazole-3-acetyl)-benzylpenicillin phenacyl ester, yield 49.4%.

Elementary analysis for $C_{30}H_{29}O_6N_3S_2$:

|  | C% | H% | N% |
|---|---|---|---|
| Found: | 61.14 | 4.83 | 7.09 |
| Calculated: | 60.91 | 4.94 | 7.10 |

EXAMPLE 26

Preparation of N-(1,2,5-thiadiazole-3-acetyl)-benzylpenicillin phenacyl ester:

Example 21 was repeated, except that potassium 1,2,5-thiadiazole-3-acetate was used in place of potassium thiophene-2-acetate, to obtain 9.13 g. of freeze-dried N-(1,2,5-thiadiazole-3-acetyl)-benzylpenicillin phenacyl ester, yield 33.3%.

Elementary analysis for $C_{28}H_{36}O_6N_4S_2$:

|  | C% | H% | N% |
|---|---|---|---|
| Found: | 57.98 | 4.45 | 9.53 |
| Calculated: | 58.13 | 4.53 | 9.68 |

EXAMPLE 27

Preparation of N-(isatin-1-acetyl)-benzylpenicillin phenacyl ester:

Example 21 was repeated except that potassium isatin-1-acetate was used in place of potassium thiophene-2-acetate, to obtain 13.08 g. of freeze-dried N-(isatin-1-acetyl)-benzylpenicillin phenacyl ester, yield 40.9%.

Elementary analysis for $C_{34}H_{29}O_8N_3S$:

|  | C% | H% | N% |
|---|---|---|---|
| Found: | 63.62 | 4.49 | 6.59 |
| Calculated: | 63.85 | 4.57 | 6.57 |

EXAMPLE 28

Preparation of N-(3-methylfurazan-4-acetyl)-benzylpenicillin phenacyl ester:

Example 21 was repeated, except that potassium 3-methylfurazan-4-acetate was used in place of potassium thiophene-2-acetate, to obtain 10.5 g. of freeze-dried N-(3-methylfurazan-4-acetyl)-benzylpenicillin phenacyl ester, yield 36.4%.

Elementary analysis for $C_{29}H_{28}O_7N_4S$:

|  | C% | H% | N% |
|---|---|---|---|
| Found: | 60.80 | 4.84 | 9.64 |
| Calculated: | 60.41 | 4.90 | 9.72 |

EXAMPLE 29

Preparation of N-(2-thienyloxyacetyl)-benzylpenicillin phenacyl ester:

Example 21 was repeated, except that potassium 2-thienyloxy acetate was used in place of potassium thiophene-2-acetate, to obtain 14.84 g. of freeze-dried N-(2-thienyloxyacetyl)-benzylpenicillin phenacyl ester, yield 50.1%.

Elementary analysis for $C_{30}H_{28}O_7N_2S_2$:

|  | C% | H% | N% |
|---|---|---|---|
| Found: | 61.10 | 4.71 | 4.71 |
| Calculated: | 60.81 | 4.76 | 4.73 |

EXAMPLE 30

Preparation of N-(3-thienyloxyacetyl)-benzylpenicillin phenacyl ester:

Example 21 was repeated, except that potassium 3-thienyloxy acetate was used in place of potassium thiophene-2-acetate, to obtain 17.42 g. of freeze-dried N-(3-thienyloxyacetyl)-benzylpenicillin phenacyl ester, yield 58.8%.

Elementary analysis for $C_{30}H_{28}O_7N_2S_2$:

|  | C% | H% | N% |
|---|---|---|---|
| Found: | 60.70 | 4.69 | 4.79 |
| Calculated: | 60.81 | 4.76 | 4.73 |

EXAMPLE 31

Preparation of N-tritylphenylglycyl-benzylpenicillin phenacyl ester:

45.2 g. (0.1 mole) of PcG phenacyl ester was dissolved in 150 ml. of dry benzene. To this solution was added 32.4 ml. (0.4 mole) of dry pyridine while cooling to 0°C. with stirring. Thereafter, a solution of 21.9 g. (0.105 mole) of $PCl_5$ in 150 ml. of dry benzene was added dropwise over a period of about 30 minutes. Subsequently, the liquid was reacted for 1 hour while manintaining the temperature thereof at 0°C.

After the reaction, precipitated pyridine hydrochloride was removed by filtration, and the reaction mother liquor was quickly washed with saturated sodium chloride solution, with saturated sodium bicarbonate solution, and with saturated sodium chloride solution to remove unreacted $PCl_5$ and by-product $POCl_3$. The washed benzene solution was dried with anhydrous silica gel, and then 40.8 g. (0.1 mole) of potassium tritylphenylglycine was added. The reaction mixture was reacted for 2 hours at 40°C.

The reaction mixture was washed with 0.5 N hydrochloric acid, with 1 N aqueous sodium bicarbonate solution, and with saturated sodium chloride solution, in this order, to remove unreacted pyridine and tritylphenylglycine, and the reaction mother liquor was dried with ahnydrous silica gel, and was then concentrated in vacuo.

Subsequently, the concentrate was charged on 500 g. of silica gel column (60 – 80 mesh) and was eluted with anhydrous benzene-ethyl acetate (10: 1), whereby the first eluted fraction contained a desired N-tritylphenyglycylbenzylpenicillin phenacyl ester. This fraction was collected and freezedried to obtain 50.6 g. of freeze-dried product, yield 61.1%.

Elementary analysis for $C_{51}H_{45}O_6N_3S$:

|  | C% | H% | N% |
|---|---|---|---|
| Found: | 75.33 | 5.65 | 4.78 |
| Calculated: | 73.98 | 5.48 | 5.07 |

EXAMPLE 32

Preparation of N-(o-nitrophenylsulfenyl phenylglycyl)benzylpenicillin phenacyl ester:

45.2 g. (0.1 mole) of the PcG phenacyl ester was dissolved in 150 ml. of dry benzene. To this solution was added 32.4 ml. (0.4 mole) of dry pyridine while cooling to 0°C. with stirring. Thereafter, a solution of 21.9 g. (0.105 mole) of $PCl_5$ in 150 ml. of dry benzene was added dropwise over a period of about 30 minutes. Subsequently, the liquid was reacted for 1 hour while maintaining the temperature thereof at 0°C.

After the reaction, precipitated pyridine hydrochloride was removed by filtration, and the reaction mother liquor was quickly washed with saturated sodium chloride solution, with saturated sodium bicarbonate solution and with saturasted sodium chloride solution, in this order. The washed benzene solution was dried with anhydrous silica gel, and then 34.2 g. (0.1 mole) of potassium o-nitrophenylsulfenyl phenylglycine was added, and was stirred at 55° – 60°C. for 5.5 hours.

The reaction liquid was washed with 0.5 N hydrochloric acid, with a 1 N aqueous sodium bicarbonate solution, and with an aqueous saturated sodium chloride solution, in this order, and the reaction mother liquor was dried with anhydrous silica gel and was then concentrated under reduced pressure. Subsequently, the concentrate was charged on a column comprising 500 g. of silica gel (60 - 80 mesh) and was eluted with anhydrous benzene-ethyl acetate (3: 1), whereby the eluted fraction contained a desired N-(o-nitrophenylsulfenyl phenylglycyl)-benzylpenicillin phenacyl ester. This fraction was collected and was freezed-dried to obtain 30.1 g. of a freeze-dried product, yield 40.8%.

Elementary analysis for $C_{38}H_{34}O_8N_4S_2$:

|  | C% | H% | N% |
|---|---|---|---|
| Found: | 61.40 | 4.66 | 7.10 |
| Calculated: | 61.78 | 4.64 | 7.58 |

EXAMPLE 33

Preparation of N-carbobenzoxyphenylglycyl benzylpenicillin phenacyl ester:

45.2 g. (0.1 mole) of PcG phenacyl ester was dissolved in 150 ml. of dry benzene. To this solution was added 32.4 ml. (0.4 mole) of dry pyridine while cooling to 0°C. with stirring. Thereafter, a solution of 21.8 g. (0.105 mole) of $PCl_5$ to 150 ml. of dry benzene was added dropwise over a period of about 30 minutes. Subsequently, the liquid was reacted for 1 hour while maintaining the temperature thereof at 0°C.

After the reaction, precipitated pyridine hydrochloride was removed by filtration, and the reaction mother liquor was quickly washed with saturated sodium chloride solution, with saturated sodium bicarbonate solution and with saturated sodium chloride solution, in this order. The washed benzene solution was dried with anhydrous silica gel, and then 32.3 g. (0.1 mole) of potassium carbobenzoxyphenylglycine was added. The reaction mixture was reacted for over night at 30°C.

The reaction mixture was washed with 0.5 N hydrochloric acid, with 1 N aqueous sodium bicarbonate solution, and with saturated sodium chloride solution, in this order, and the reaction mother liquer was dried with anhydrous silica gel, and was then concentrated in vacuo.

Subsequently, the concentrate was charged on 500 g. of silica gel column (60 - 80 mesh) and was eluted with anhydrous benzeneethyl acetate (10: 1), whereby the first eluted fraction contained a desired N-carbobenzoxy phenylglycyl penicillin phenacyl ester. This fraction was collected and freeze-dried to obtain 42.5 g. of freeze-dried product, yield 59.0%.

Elementary analysis for $C_{40}H_{37}O_8N_3S$:

|  | C% | H% | N% |
|---|---|---|---|
| Found: | 66.70 | 5.04 | 5.86 |
| Calculated: | 66.75 | 5.18 | 5.84 |

Having described our invention we claim:

1. A process for the production of a diacyl penicillin, comprising admixing 1 mole of a benzyl penicillin ester of the formula

[chemical structure: phenyl-$CH_2$—CO—NH—CH—CH, S, C($CH_3$)($CH_3$), O=C—N—CH—COOX]

wherein X is phenacyl, with 1–2 moles of a chlorinating agent selected from the group consisting of $PCl_5$, $POCl_3$, $COCl_2$ and $SOCl_2$, and 1–5 moles of a tertiary organic amine selected from the group consisting of pyridine, quinoline and dimethylaniline, at a temperature of −20° to 25°C., to obtain an imide chloride group-incorporated compound of the formula

[chemical structure: phenyl-$CH_2$—C(Cl)=N—CH—CH, S, C($CH_3$)($CH_3$), O=C—N—CH—COOX]

wherein X is phenacyl; and then admixing one mole of the compound of the last-named formula with 1-2 moles of a carboxylate of the formula $$R-\underset{\underset{O}{\|}}{C}-OM$$

wherein M is a metal atom selected from the group consisting of potassium, sodium, lithium and silver, and R is a member selected from the group consisting of 1-(2′,6′-dichlorophenyl)4-methylpyrazole-5-carbonyl, 1-(p-chlorophenyl)-3-methylpyrazole5-carbonyl, and 1-phenyl-4-methylpyrazole-5-carbonyl, at a temperature of 20° to 60°C.

2. N-[1-(2′,6′-dichlorophenyl)-4-methylpyrazole-5-carbonyl]-benzylpenicillin phenacyl ester.

3. N-[1-(p-chlorophenyl)-3-methylpyrazole-5-carbonyl]benzylpenicillin phenacyl ester.

4. N-(1-phenyl-4-methylpyrazole-5-carbonyl)-benzylpenicillin phenacyl ester.

* * * * *